United States Patent [19]

Hunter

[11] Patent Number: 4,924,013
[45] Date of Patent: May 8, 1990

[54] PROCESS FOR THE REDUCTION OF FREE EPICHLOROHYDRIN IN EPOXY COMPOUNDS

[75] Inventor: Joe M. Hunter, Fern Creek, Ky.

[73] Assignee: Hi-Tek Polymers, Inc., Jeffersontown, Ky.

[21] Appl. No.: 222,794

[22] Filed: Jul. 22, 1988

[51] Int. Cl.$^5$ .................. C07D 301/27; C07D 301/32
[52] U.S. Cl. .................................... 549/514; 549/515; 549/516; 549/517; 549/541
[58] Field of Search ............... 549/514, 515, 516, 517, 549/541

[56] References Cited

U.S. PATENT DOCUMENTS 2,682,547  6/1954  Clemens et al. ............... 549/517
2,841,595  7/1958  Pezzaglia ....................... 549/517
4,785,061 11/1988  Wang et al. .................... 549/541

Primary Examiner—Richard L. Raymond
Assistant Examiner—Ba K. Trinh
Attorney, Agent, or Firm—Herbert P. Price

[57] ABSTRACT

A process for the reduction of free epichlorohydrin in epoxy compounds which involves the treatment of an epoxy compound with an alkali metal sulfite, preferably sodium sulfite.

17 Claims, No Drawings

PROCESS FOR THE REDUCTION OF FREE EPICHLOROHYDRIN IN EPOXY COMPOUNDS

BACKGROUND OF THE INVENTION

The field of art to which this invention pertains is epoxy compounds and a process for reducing the amount of free epichlorohydrin in epoxy compounds.

The preparation of epoxy compounds by the reaction of epichlorohydrin with monocarboxylic or polycarboxylic acids, monohydric or polyhydric alcohols, and monohydric or polyhydric phenols is well known. Such compounds are usually prepared by reacting epichlorohydrin with an alcohol or acid to form a chlorohydrin ether or ester followed by the dehydrohalogenation of the ether or ester to form an epoxy compound. However, when a phenol is employed, the phenol is usually reacted with excess epichlorohydrin in the presence of sodium hydroxide so that condensation and dehydrohalogenation occurs concomitantly.

The employment of the prior art processes for preparing such epoxy compounds results in the presence of some free epichlorohydrin in the compounds, even though an attempt is usually made to reduce the amount of residual epichlorohydrin. The presence of free epichlorohydrin is undesirable because epichlorohydrin is toxic and is a contaminate in the compound. Generally, the prior art processes attempt to remove residual unreacted epichlorohydrin by distillation and/or by extraction with $H_2O$. See, for example, U.S. Pat. No. 3,859,314. However, the use of distillation, washing or other prior art means for reducing the amount of residual free epichlorohydrin still leaves relatively high amounts of free epichlorohydrin in the epoxy compound.

As a result, it is an object of this invention to reduce the amount of free epichlorohydrin in epoxy compounds.

It is another object of this invention to reduce the amount of free epichlorohydrin in epoxy compounds to a greater degree than is possible using the prior art methods for reducing free epichlorohydrin.

It is a further object of this invention to inexpensively and easily reduce the amount of residual epichlorohydrin in epoxy compounds.

These objects are obtained by the process of this invention.

SUMMARY OF INVENTION

This invention relates to epoxy compounds. In one respect, this invention pertains to glycidyl ethers and esters. In another aspect, this invention relates to epoxy compounds containing residual epichlorohydrin. The process for reducing residual epichlorohydrin in an epoxy compound prepared by reacting epichlorohydrin with an alcohol, phenol or carboxylic acid comprises the steps of:

(a) adding an alkali metal sulfite to the epoxy compound;

(b) mixing water, the alkali metal sulfite and the epoxy compound; and (c) separating the epoxy compound from water, unreacted alkali metal sulfite, and sulfite by-products.

DESCRIPTION OF INVENTION

The process of this invention can be employed with any epoxy compound prepared by the reaction of epichlorohydrin with a monohydric or polyhydric alcohol, a monohydric or polyhydric phenol, or a monocarboxylic or polycarboxylic acid.

The monohydric alcohols from which epoxy compounds suitable for use in the present process may be derived include alcohols such as ethyl, propyl and butyl alcohols, etc., or higher alcohols such as lauryl or soya alcohols, etc.

The polyhydric alcohols from which suitable epoxy compounds may be derived include glycols and polyglycols containing at least two hydroxyl groups, such as ethylene glycol, butanediol, pentanediol, diethylene glycol, triethylene glycol, hexanetriol, glycerol, trimethylol ethane, trimethylol propane, pentaerythritol and various polyethylene glycols and polypropylene glycols, etc.

Other polyhydric alcohols include castor oil, dihydroxy alkyl ethers of dihydric phenols, e.g., the dihydroxyethyl ethers of bisphenol, resorcinol, etc.

The monohydric and polyhydric phenols from which suitable epoxy compounds may be derived include phenol, ortho, meta and para cresol, resorcinol, hydroquinone, p,p'-dihydroxydiphenyl propane, dihydroxybenzo- phenone, dihydroxydiphenyl sulfone, dihydroxynaphthalene, and novolak resins which are the non-heat reactive reaction products of phenols with aldehydes, such as phenol plus formaldehyde. The preferred phenols are dihydric phenols and most preferably p,p'-dihydroxydiphenyl propane, commonly called Bisphenol A.

The monocarboxylic acids from which suitable epoxy compounds may be derived contain from 2 to about 24 carbon atoms, such as acetic acid, hexanoic acid, steric acid and acids derived from vegetable oils.

The polycarboxylic acids can be aliphatic, cycloaliphatic, aromatic and heterocyclic. The preferred acids are those which contain not more than about 18 carbon atoms per carboxylic acid group. Examples of suitable acids include oxalic acid, sebacic acid, adipic acid, succinic acid, pimelic acid, suberic acid, glutaric acid, dimer and trimer acids of unsaturated fatty acid, such as dimer and trimer acids of linseed fatty acids, phthalic acid, isophthalic acid, terephthalic acid, trimellitic acid, trimesic acid, phenylene-diacetic acid, chlorendic acid, hexahydrophthalic acid, diphenic acid, naphthalic acid, polyacid terminated esters of dibasic acids and aliphatic polyols, polymers and copolymers of acrylic acid, methacrylic acid, crotonic acid, and the like.

The preparation of the epoxy compounds suitable for use in this invention is well known in the art. For example, U.S. Pat. Nos. 3,033,803, 3,351,574, 3,404,126 and 3,859,314 disclose, respectively, the preparation of glycidyl ethers of monohydric and polyhydric phenols, castor oil polyglycidyl ethers, glycidyl ethers of polyhydric phenols, and glycidyl esters of polycarboxylic acids. These patents are incorporated herein by reference, and the epoxy compounds disclosed therein are suitable for use in the present invention. Most preferably, the epoxy compound employed is a castor oil polyglycidyl ether or a butyl glycidyl ether.

The general process for preparing suitable epoxy compounds is as follows. First, an alcohol is reacted with epichlorohydrin in the presence of a condensation catalyst, such as boron trifluoride, to form a chlorohydrin ether. Second, the catalyst is deactivated. Third, the chlorohydrin ether is reacted with a dehydrohalogenating agent, such as sodium hydroxide, to produce a glycidyl ether. After dehydrohalogenation, there are two phases: an organic phase containing the compound and a water phase containing salt by-products of dehydrohalogenation. The water phase is drawn off and a water immiscible solvent, usually methylisobutylketone, is added. The solvent helps to reduce the viscosity of the resin thereby making it easier to handle and to separate. The resin is then water washed to remove the remaining salt by-products of dehydrohalogenation and to reduce the amount of residual epichlorohydrin. Finally, the solvent and water are removed, such as by distillation.

Phenols and acids are generally condensed with epichlorohydrin and dehydrohalogenation in excess epichlorohydrin. After the dehydrohalogenation, the excess epichlorohydrin is removed by distillation, and water is added to dissolve the salt formed in the dehydrohalogenation reaction. The removal of salt, solvent and water is conducted as described above.

The epichlorohydrin containing epoxy compound can be treated with an alkali metal sulfite to reduce the amount of free epichlorohydrin either during or after processing. However, it is preferred that the treatment with sulfite be performed during processing. Generally, this means that the sulfite treatment will take place immediately after dehydrohalogenation or after an initial washing of the compound after dehydrohalogenation.

The suitable sulfites are alkali metal sulfites, preferably sodium sulfite ($Na_2SO_3$) or potassium sulfite ($K_2SO_3$), and most preferably sodium sulfite. The amount of alkali metal sulfite added to the compound will be in the range of about 2 to about 15 percent by weight based upon the weight of the compound, and most preferably in the range of about 5 to about 8 percent by weight. If the brine solution containing the salt by-product of dehydrohalogenation is still in the reaction vessel, the sulfite may be added in solid form. However, it is generally preferred to dissolve the sulfite in water prior to treating the compound with the alkali metal sulfite. The amount of water employed is not critical.

After the alkali metal sulfite is added, the epoxy compound, water and sulfite are mixed by stirring or agitation. Generally, they are stirred or agitated for a period of time in the range of about 1 hour to about 4 hours and preferably about 2 to about 3 hours. The temperature at which they are stirred or agitated can be in the range of room temperature to the boiling point of water since the alkali metal sulfite is dissolved in water. As a result, the temperature is usually in the range of room temperature to about 212° F. It is preferred to use heat because the reaction between the sulfite ion and the free epichlorohydrin proceeds faster and because the epoxy compound is less viscous.

If an already prepared epoxy compound is to be treated, such as a commercially obtained compound, the alkali metal sulfite is dissolved in water, added to the compound, and then stirred and heated as indicated above. (If the epoxy compound is quite viscous, a water immiscible solvent, such as methylisobutyl ketone, can be added to facilitate stirring).

After the compound, water and alkali metal sulfite have been stirred or agitated together for an appropriate time, the epoxy compound is separated from the water, unreacted alkali metal sulfite and sulfite by-products. This is done by first stopping the stirring or agitating so that the mixture can separate into layers. The layer not containing the epoxy compound is then drawn off. Next, the water immiscible compound solvent is removed from the layer containing the compound by any suitable means, such as vacuum distillation. The conditions for removal will depend on the particular compound and solvent involved, and one skilled in the art will readily know the appropriate conditions for stripping the solvent. After the solvent is removed, the compound can be filtered.

The process of this invention can be employed to remove free epichlorohydrin which contaminates many epoxy compounds. Removal of epichlorohydrin from such compounds will decrease the adverse effects that residual epichlorohydrin have upon products prepared from the compounds as well as remove a toxic contaminate. Generally, treatment of a compound to remove residual epichlorohydrin does not adversely affect the properties of the compound.

The invention is illustrated by the following examples in which all parts and percentages are by weight unless otherwise indicated.

EXAMPLE 1

To a 5 liter flask equipped with stirrer, thermometer, condenser and addition tube were added 904.2 parts of castor oil and 2.8 parts of $BF_3$ etherate (47% $BF_3$). The solution was heated to about 182° F. where dropwise addition of 312 parts of epichlorohydrin was begun. The epichlorohydrin was added over a period of 2½ hours with the temperature being controlled between about 182° F. and about 197° F. by external cooling and the rate of epichlorohydrin addition. In order to deactivate the $BF_3$ catalyst, 11.2 parts of 50 percent sodium hydroxide and water were added and the reaction mixture was allowed to cool to room temperature.

Next, 795 parts of epichlorohydrin were added and the reaction mixture was heated to about 161° F. under a vacuum pressure of about 140 mm of Hg to distill out water. The reactants were heated for about 30 minutes. Subsequently, 128 parts of anhydrous sodium hydroxide were added at the rate of 10.7 grams every 15 minutes. After all the sodium hydroxide was added, the mixture was held at about 160° F. for one half hour at which point 13.3 parts of demineralized water were added. After 5 minutes, the water was removed by azeotrope vacuum distillation at about 40 mm of Hg and under heat. When the temperature reached about 300° F., the reaction mixture was held at that temperature for about 30 minutes to strip off epichlorohydrin. A sample of the compound was then removed.

Next, 200 parts of methylisobutylketone (MIBK) were added along with 595 parts of water and 60 parts of sodium sulfite. The mixture was heated to reflux, and 200 parts of demineralized water were added to solubilize the salt. After about an hour, stirring was stopped to allow for the layers to separate. The bottom brine layer was then drawn off. At a pressure of about 40 mm of Hg and a temperature of about 300° F., the remaining solvent was vacuum distilled for about 30 minutes. The compound was allowed to cool to about 250° F. under vacuum, then the vacuum was broken with nitrogen and the compound was filtered through a Buchner funnel to yield about 1154 parts of a castor oil glycidyl ether. The amount of free epichlorohydrin in the sample obtained before the sulfite treatment and in the compound treated with sulfite was determined by gas chromatagraph analysis. The untreated compound contained about 2700 ppm epichlorohydrin and the treated compound contained about 18 ppm.

EXAMPLE 2

Example 1 was repeated except that sodium sulfite was not added. In other words, the compound was washed with water. The resulting compound had about 903 ppm epichlorohydrin.

EXAMPLE 3

971.3 parts of Epi-Rez 505, which is a polyglycidyl ether of castor oil and is commercially available from Interez, Inc., was placed in a 2 liter round bottom flask and heated to about 200° F. 37.1 parts of sodium sulfite were added and then 491.7 parts water. The mixture was heated to 210° F. and held there for about 60 minutes. The agitation was stopped so that separation could occur. 682.9 parts of the aqueous layer were drawn off. The remaining compound was heated to 300° F. under vacuum and held at about 40 mm of Hg for about 10 minutes. The compound was held under vacuum until the temperature reached 240° F. at which point the vacuum was broken and the compound was filtered through a Buchner funnel. When tested by gas chromatography for residual epichlorohydrin, the amount of residual epichlorohydrin was about 1 ppm. An untreated sample of Epi-Rez 505 contained about 145 ppm epichlorohydrin.

EXAMPLE 4

Example 3 was repeated except that potassium sulfite was used instead of sodium sulfite. The resulting treated compound had about 42 ppm epichlorohydrin.

EXAMPLE 5

600 parts of Epi-Rez 501, which is a butyl glycidyl ether commercially available from Interez, Inc., were added to a 2 liter flask along with 855 parts of water and 285 parts of sodium chloride. The water and salt were added in order to achieve a mixture approximating the mixture present after dehydrohalogenation when the compound was first prepared. The mixture was stirred and heated to about 180° F. 120 parts of water and 30 parts of sodium sulfite were premixed and then added. The mixture was held at 180° F. for about 1 hour, at which time stirring was stopped in order to allow for phase separation. The bottom brine level was drawn off. Then under vacuum, the remaining layer containing the compound was heated to about 180° F. under 1.8 inches of Hg in order to remove residual solvent. After about 25 minutes, the vacuum was broken and the compound was filtered. The compound was tested for free epichlorohydrin by gas chromatography. The sample contained less than 1 ppm of free epichlorohydrin whereas an untreated sample of Epi-Rez 501 contained about 56 ppm of epichlorohydrin.

EXAMPLE 6

Example 5 was repeated except that the 120 parts of water and 30 parts of sodium sulfite were not added. In other words, the compound was simply washed with a brine solution under the same conditions as in Example 5. When the compound was tested for free epichlorohydrin, it contained about 36 ppm of epichlorohydrin.

The examples demonstrate that the treatment of an epichlorohydrin containing compound with an alkali metal sulfite dramatically reduces the amount of free epichlorohydrin in the compound and that the use of alkali metal sulfites reduces the amount of free epichlorohydrin more than the use of prior art methods, such as water washing and vacuum distillation.

What is claimed:

1. A process for the reduction of free epichlorohydrin in an epoxy compound prepared by reacting epichlorohydrin with an alcohol, phenol or carboxylic acid which comprises the steps of:
   (a) adding an alkali metal sulfite to the epoxy compound;
   (b) mixing water, the alkali metal sulfite and the epoxy compound; and
   (c) separating the epoxy compound from the water, unreacted alkali metal sulfite, and sulfite by-products.

2. The process of claim 1 wherein the alkali metal sulfite is sodium sulfite or potassium sulfite.

3. The process of claim 1 wherein the alkali metal sulfite is sodium sulfite.

4. The process of claim 1 wherein the alkali metal sulfite and the epoxy compound are mixed at a temperature in the range of about room temperature to about 212° F.

5. The process of claim 1 wherein the alkali metal sulfite and the epoxy compound are mixed for a period of time in the range of about 1 hour to about 4 hours.

6. The process of claim 1 wherein the alkali metal sulfite and the epoxy compound are mixed for a period of time in the range of about 2 to about 3 hours.

7. The process of claim 1 wherein the epoxy compound is a castor oil polyglycidyl ether or a butyl glycidyl ether.

8. The process of claim 1 wherein the alkali metal sulfite is dissolved in water prior to being added to the epoxy compound.

9. A process for the reduction of free epichlorohydrin in an epoxy compound prepared by reacting epichlorohydrin with an alcohol, phenol or carboxylic acid which comprises the steps of:
   (a) adding about 2 to about 15 percent by weight alkali metal sulfite to the epoxy compound;
   (b) mixing water, the alkali metal sulfite and the epoxy compound; and
   (c) separating the epoxy compound from the water, unreacted alkali metal sulfite, and sulfite by-products.

10. The process of claim 9 wherein the alkali metal sulfite is sodium sulfite or potassium sulfite.

11. The process of claim 9 wherein the alkali metal sulfite is sodium sulfite.

12. The process of claim 9 wherein about 5 to about 8 percent by weight alkali metal sulfite is added.

13. The process of claim 9 wherein the alkali metal sulfite and the epoxy compound are mixed at a temperature in the range of about room temperature to about 212° F.

14. The process of claim 9 wherein the alkali metal sulfite and the epoxy compound are mixed for a period of time in the range of about 1 hour to about 4 hours.

15. The process of claim 9 wherein the alkali metal sulfite and the epoxy compound are mixed for a period of time in the range of about 2 to about 3 hours.

16. The process of claim 9 wherein the epoxy compound is a castor oil polyglycidyl ether or a butyl glycidyl ether.

17. The process of claim 9 wherein the alkali metal sulfite is dissolved in water prior to being added to the epoxy compound.

* * * * *